(12) United States Patent
Byun et al.

(10) Patent No.: US 8,088,753 B2
(45) Date of Patent: Jan. 3, 2012

(54) HEPARIN CONJUGATES AND METHODS

(75) Inventors: Youngro Byun, Seoul (KR); E Sak Lee, Seoul (KR); Ok-cheol Jeon, Seoul (KR); Sang Yoon Kim, Seoul (KR); Rang-Woon Park, Dae gu (KR)

(73) Assignee: Mediplex Corporation, Korea, Seoul (KR)

( * ) Notice: Subject to any disclaimer, the term of this patent is extended or adjusted under 35 U.S.C. 154(b) by 424 days.

(21) Appl. No.: 12/188,138

(22) Filed: Aug. 7, 2008

(65) Prior Publication Data

US 2009/0149424 A1 Jun. 11, 2009

Related U.S. Application Data

(63) Continuation-in-part of application No. 11/824,594, filed on Jun. 29, 2007, now abandoned.

(51) Int. Cl.
*A61K 31/727* (2006.01)
*A61K 31/575* (2006.01)
*A61K 31/50* (2006.01)

(52) U.S. Cl. ........... 514/56; 514/169; 514/171; 514/249

(58) Field of Classification Search ........................ None
See application file for complete search history.

(56) References Cited

U.S. PATENT DOCUMENTS

| | | | |
|---|---|---|---|
| 5,474,765 A * | 12/1995 | Thorpe | ...................... 424/78.17 |
| 6,245,753 B1 | 6/2001 | Byun | |
| 6,589,943 B2 | 7/2003 | Byun | |
| 6,656,922 B2 | 12/2003 | Byun | |
| 6,702,850 B1 | 3/2004 | Byun | |
| 7,129,224 B1 | 10/2006 | Byun | |

FOREIGN PATENT DOCUMENTS

WO WO 2006/042146 * 4/2006

OTHER PUBLICATIONS

Thomas, A. et al "Targeted delivery of heparin and LMWH . . . " Atherosclerosis (2004) vol. 176, pp. 73-81.*
Meddahi, A. et al "FGF protection and inhibition of human neutrophil elastase . . . " Int. J. Biol. Macromol. (1996) vol. 18, pp. 141-145.*
Gittens, S. et al "Imparting bone mineral affinity to osteogenic proteins . . . " J. Controlled Release (2004) vol. 98, pp. 255-268.*
Suh, H. et al "Anti-angiogenic actiivity of ursodeoxycholic acid . . . " Cancer Lett. (1997) vol. 113, pp. 117-122.*
Alberts, D. et al "Phase III trial of ursodeoxycholic acid . . . " JNCI (2005) vol. 97, No. 11, pp. 846-853.*
Soma, T. et al "Chenodeoxycholic acid stimulates the progression of human esophageal cancer cells . . . " Int. J. Cancer (2006) vol. 119, 771-782.*
Kyeongsoon Park et al., Preparation and Characterization of Self-Assembled Nanoparticles of Heparin-Deoxycholic Acid Conjugates, 20 Langmuir 11726-11731 (2004).
Kyeongsoon Park et al., Antiangiogenic Effect of Bile Acid Acylated Heparin Derivative, 24 Pharmaceutical Research 176-185 (2007).
Kyeongsoon Park et al., Heparin-deoxycholic acid chemical conjugate as an anticancer drug carrier and its antitumor activity, 114 Journal of Controlled Release 300-306 (2006).
Mi Kyung Yu et al., Antiangiogenic and Apoptotic Properties of a Novel Amphilphilic Folate-Heparin-Lithocholate Derivative Having Cellular Internality for Cancer Therapy, 24 Pharmaceutical Research 705-714 (2007).

* cited by examiner

*Primary Examiner* — Leigh Maier

(74) *Attorney, Agent, or Firm* — Clayton, Howarth & Cannon, P.C.

(57) ABSTRACT

Heparin conjugates and methods of making and use thereof are disclosed. An illustrative heparin conjugate includes a composition wherein a bile acid is bonded to heparin through the 3-carbon of the bile acid. A spacer may be interposed between the bile acid and the heparin. Another embodiment includes a targeting moiety bonded to the heparin-bile acid conjugate through a spacer. Another illustrative heparin conjugate includes heparin covalently bonded to a sulfonated moiety, such as a naphthalene trisulfonate residue. A method of treating cancer includes administering a heparin conjugate to an individual in need thereof.

18 Claims, 11 Drawing Sheets

HEPARIN CONJUGATES AND METHODS

CROSS-REFERENCE TO RELATED APPLICATIONS

This application is a continuation-in-part of U.S. application Ser. No. 11/824,594, filed Jun. 29, 2007.

STATEMENT REGARDING FEDERALLY SPONSORED RESEARCH OR DEVELOPMENT

Not applicable.

BACKGROUND OF THE INVENTION

This invention relates to heparin conjugates and methods of making and using thereof. More particularly, this invention relates to heparin-bile acid conjugates, heparin-bile acid conjugates further including a targeting moiety, heparin-bile acid conjugates wherein the heparin is bonded to the bile acid through the 3-carbon of the bile acid, and heparin conjugates wherein heparin is covalently bonded to sulfonated moieties. Methods of using these conjugates for treating cancer are also described.

Heparin, due to its heterogeneous structure, can interact with many kinds of proteins. Heparin has anti-tumoral and anti-inflammatory activities as well as its well known anti-coagulant activity. R. Sasisekharan et al., Roles of heparan-sulphate glycosaminoglycans in cancer, 2 Nat. Rev. Cancer 521-528 (2002). Among the many sorts of proteins that interact with heparin are growth factors, which are key regulators for cell mitogenic activity. Growth factors usually bind with growth factor receptors and can modulate cell growth. In particular, vascular endothelial growth factor (VEGF) is a key protein in physiological angiogenesis (or neo-vascularization), or formation of new blood vessels. N. Ferrara et al., The biology of VEGF and its receptors, 9 Nat. Med. 669-676 (2003). Angiogenesis is a complex multi-step process involving endothelial cell activation, controlled proteolytic degradation of the extracellular matrix (ECM), proliferation and migration of endothelial cells, and formation of capillary vessel lumina. Diaz-Flores et al., 33 Anat. Histol. Embryol. 334-338 (2004).

Binding of growth factors to heparins or heparan sulfates is thought to have a crucial role in the modulation of activity of the high-affinity receptors. S. Colin et al., In Vivo Involvement of Heparan Sulfate Proteoglycan in the Bioavailability, Internalization, and Catabolism of Exogenous Basic Fibroblast Growth Factor, 55 Mol. Pharmacol. 74-82 (1999); I. J. Mason, The Ins and Outs of Fibroblast Growth Factors, 78 Cell 547-552 (1994); S. Tessler et al., Heparin Modulates the Interaction of VEGF165 with Soluble and Cell Associated flk-1 Receptors, 269 J. Biol. 12456-12461 (1994). Unfractionated heparin (UFH) or heparan sulfates promote basic fibroblast growth factor (bFGF) receptor dimerization and activation, thus enhancing cell growth. J. Schlessinger et al., Regulation of Growth Factor Activation by Proteoglycans: What Is the Role of the Low Affinity Receptors?, 83 Cell 357-360 (1995). Interestingly, it has been shown that low molecular weight heparin (LMWH; MW =4500-6000 Da), in contrast to UFH, can hinder binding of growth factors to their high-affinity receptors as a result of its smaller size. Indeed, in vitro heparin fragments of less than 18 saccharide residues reduce activity of VEGF, and fragments of less than 10 saccharide residues inhibit activity of bFGF. G. C. Jayson et al., Heparin Oligosaccharides: Inhibitors of the Biological Activity of bFGF on Caco-2 Cells, 75 Br. J. Cancer 9-16 (1997); S. Soker et al., Variations in the Size and Sulfation of Heparin Modulate the Effect of Heparin on the Binding of VEGF165 to its Receptors, 203 Biochem. Biophys. Res. Comm. 1339-1347 (1994).

Many anti-cancer drugs were designed as inhibitors of VEGF and its receptors. Bevacizumab (Avastin®) is an FDA-approved, anti-angiogenic drug that is representative of such VEGF inhibitors. Bevacizumab is a basic monoclonal antibody that binds the negatively charged receptor binding domain of VEGF and, therefore, can block the interaction between VEGF and VEGF receptors (Flk1, KDR). L. M. Ellis, Mechanisms of Action of Bevacizumab as a Component of Therapy for Metastatic Colorectal Cancer, 33 Semin. Oncol. S 107 (2006); E. Bergsland & M. N. Dickler, Maximizing the Potential of Bevacizumab in Cancer Treatment, 9 Oncologist 36-42 (2004).

LMWH can bind the heparin binding domain of VEGF. The sulfate groups of heparin can bind with positively charged amino acid residues, such as arginine, histidine, and lysine. A model of complexes formed between the heparin binding domain of VEGF and heparin or heparan sulfate predicts that sulfate and carboxylate groups of heparin contact these basic amino acid residues in the heparin-binding cleft of the VEGF protein. C. J. Robinson et al., VEGF165-binding sites within heparan sulfate encompass two highly sulfated domains and can be liberated by K5 lyase, 281 J. Biol. Chem. 1731-1740 )2006). However, there is no evidence that binding of heparin to VEGF results in an anti-angiogenic effect. Treatment of VEGF with either UFH or LMWH had no effect on tumor-associated angiogenesis in an experimental model of colon cancer metastasis in rat liver. S. M. Smorenburg et al., In Vivo Treatment of Rats with Unfractionated Heparin (UFH) or Low Molecular Weight Heparin (LMWH) Does Not Affect Experimentally Induced Colon Carcinoma Metastasis, 17 Clin. Exp. Metastasis 451-456 (1999).

VEGF comprises two main parts, a positively charged heparin binding domain (HBD; amino acid residues 111-165) and a negatively charged receptor binding domain (RBD; amino acid residues 8-109). B. A. Keyt et al., Identification of Vascular Endothelial Growth Factor Determinants for Binding KDR and FLT-1 Receptors. Generation of Receptor-selective VEGF Variants by Site-directed Mutagenesis, 271 J. Biol. Chem. 5638-56-46 (1996). Because HBD and RBD are in separate domains, even though heparin binds with HBD, the RBD maintains its structure.

It has been reported that HBD-deleted VEGF can bind to the VEGF receptor, but mitogenic activity is absent. B. A. Keyt et al., The carboxyl-terminal domain (111-165) of vascular endothelial growth factor is critical for its mitogenic potency, 271 J. Biol. Chem. 7788-7795 (1996). Thus, it was concluded that the HBD is critical to the cell growth activity of VEGF. RBD binding to VEGF cannot maintain cell growth.

In vitro experiments have suggested that the VEGF HBD-mediated interaction with neuropilin-1 (NP-1) increases the affinity of VEGF for KDR (VEGF receptor 2). Furthermore, the affinity of VEGF for the NP-1 extracellular domain is greatly enhanced by the addition of heparin. These results suggest that heparin mediates a successful interaction between VEGF and the receptor. H. Jia et al., Characterization of a Bicyclic Peptide Neuropilin-1 (NP-1) Antagonist (EG3287) Reveals Importance of Vascular Endothelial Growth Factor Exon 8 for NP-1 Binding and Role of NP-1 in KDR Signaling, 281 J. Biol. Chem. 13493-13502 (2006).

Finally, the VEGF receptor is a monomer before binding with the RBD of VEGF. When a VEGF ligand binds with the monomer receptor, then receptor dimerization can be initiated. After dimerization, two domains of the receptor experience conformational changes, resulting in a coiled structure. After all these steps, angiogenic signaling occurs. C. Ruch et al., Structure of a VEGF-VEGF receptor complex determined by electron microscopy, 14 Nat. Struct. Mol. Biol. 249-250 (2007).

BRIEF SUMMARY OF THE INVENTION

An illustrative embodiment according to the present invention comprises a composition represented by the formula

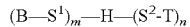
$(B-S^1)_m-H-(S^2-T)_n$ wherein B is a bile acid residue or a bile acid analog, H is a heparin residue, $S^1$ is a first spacer, $S^2$ is a second spacer, T is a targeting moiety, m is an integer of about 0 to about 50, and n is an integer of 0 to about 10, with the proviso that both m and n cannot be 0, wherein B and $S^1$ are bonded to each other through a 3-carbon of B, and $S^1$ and $S^2$ can be the same or different. In another illustrative embodiment of the invention, m is about 1 to about 30. In still another illustrative embodiment of the invention, m is about 1 to about 10. In yet another illustrative embodiment of the invention, n is about 1 to about 10.

The bile acid residue may be selected, for example, from the group consisting of residues of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid. The heparin can comprise heparin of any type, such as unfractionated heparin, high molecular weight heparin, low molecular weight heparin, heparin fragments, recombinant heparin, heparin analogs, heparan sulfate, and sulfonated polysaccharides containing heparin activity, and the like. The spacer can comprise an alkyl chain, polyethylene glycol, an ethylene diamine residue, and the like. The targeting moiety may comprise a folic acid residue, a cRGD residue, and the like. An illustrative composition according to the present invention comprises a composition wherein B is a taurocholate residue, H is a low molecular weight heparin residue, $S^1$ and $S^2$ are ethylene diamine residues, and T is a cRGD residue. Another illustrative composition according to the present invention comprises a composition wherein B is a lithocholate residue, H is a low molecular weight heparin residue, $S^1$ and $S^2$ are ethylene diamine residues, and T is a folate residue.

Another illustrative embodiment according to the present invention comprises a composition comprising at least one sulfonated moiety, such as naphthalene trisulfonate, covalently bonded to heparin. Other illustrative embodiments comprise compositions wherein analogs of naphthalene trisulfonate or sulfonated naphthalenes are substituted for naphthalene trisulfonate.

Still another illustrative embodiment according to the present invention comprises a composition comprising heparin bonded to the 3-carbon of a bile acid or bile acid analog. Illustratively, the bile acid analog comprises a sulfonate group. The composition may further comprise a spacer between heparin and the bile acid or bile acid analog, such as an ethylene diamine residue, an alkyl chain, polyethylene glycol, and the like. The composition may also further comprise a targeting moiety coupled to the heparin through a second spacer.

Yet another illustrative embodiment of the invention comprises a method of treating cancer comprising administering to an individual in need thereof an effective amount of a composition represented by the formula

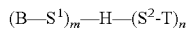
$(B-S^1)_m-H-(S^2-T)_n$ wherein B is a bile acid residue or a bile acid analog, H is a heparin residue, $S^1$ is a first spacer, $S^2$ is a second spacer, T is a targeting moiety, m is an integer of about 0 to about 50, and n is an integer of 0 to about 10, with the proviso that m and n cannot both be 0, and wherein B and $S^1$ are bonded to each other through a 3-carbon of B, and $S^1$ and $S^2$ can be the same or different.

Still another illustrative embodiment of the invention comprises a method of treating cancer comprising administering to an individual in need thereof an effective amount of a composition comprising heparin bonded to the 3-carbon of a bile acid or bile acid analog.

Another illustrative embodiment of the invention comprises a method of making a heparin-spacer-bile acid or heparin-spacer-bile acid analog conjugate. The method comprises activating the 3-carbon of a bile acid or bile acid analog to result in an activated bile acid or activated bile acid analog, bonding a first spacer to the activated bile acid or activated bile acid analog to result in a spacer-bile acid or spacer-bile acid analog, activating a heparin to result in an activated heparin, and then bonding the activated heparin to the spacer-bile acid or spacer-bile acid analog to result in the heparin-spacer-bile acid or heparin-spacer-bile acid analog conjugate. Still another illustrative embodiment of the invention comprises a method of making a heparin-spacer-bile acid-spacer-targeting moiety or heparin-spacer-bile acid analog-spacer-targeting moiety conjugate. The method comprises activating the targeting moiety to result in an activated targeting moiety, bonding a second spacer to the activated targeting moiety to result in a second spacer-targeting moiety, and then bonding the second spacer-targeting moiety to a heparin-spacer-bile acid conjugate or heparin-spacer-bile acid analog conjugate to result in the heparin-spacer-bile acid-spacer-targeting moiety conjugate or heparin-spacer-bile acid analog-spacer-targeting moiety conjugate.

DETAILED DESCRIPTION

Figure 1:
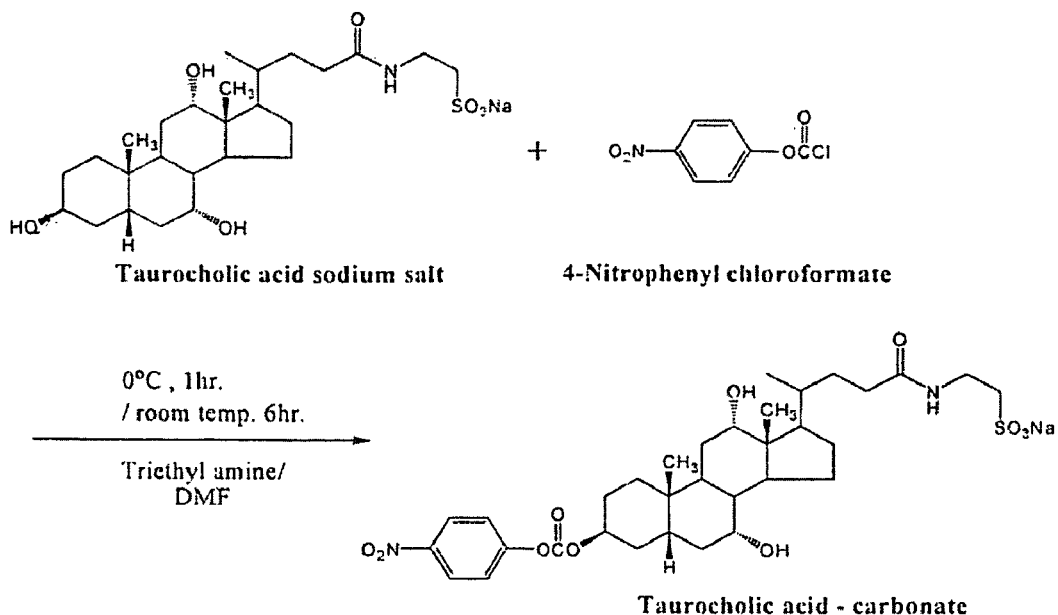
FIG. 1 illustrates a scheme for synthesis of taurocholic acid carbonate derivative (CB-TCA) by reaction of taurocholic acid sodium salt with 4-nitrophenyl chloroformate such that the 4-nitrophenyl formate group bonds to the 3-hydroxy group of taurocholic acid.

Before the present heparin-bile acid conjugates and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "bile acids" means natural and synthetic derivatives of the steroid, cholanic acid, including, without limitation, cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof, and the like. The carbon atoms in a bile acid are numbered according to the standard numbering system used for steroids, which is well known in the art. R. T. Morrison & R. N. Boyd, *Organic Chemistry* 514 (3d ed. 1973). Thus, the 3-carbon of a bile acid is contained in the A ring thereof. Bile acid analogs can also be used according to the present invention. Examples of such bile acid analogs include bile acids bearing at least one sulfonate group.

As used herein, "effective amount" means an amount of a heparin conjugate that is nontoxic but sufficient to provide the desired effect and performance at a reasonable benefit/risk ratio attending any cancer treatment.

As used herein, "administering" and similar terms mean delivering the composition to the individual being treated such that the composition is capable of being circulated systemically to the parts of the body where cancer cells are located. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

An illustrative embodiment according to the present invention comprises a composition represented by the formula

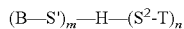

$$(B-S^1)_m-H-(S^2-T)_n$$

wherein B is a bile acid residue or a bile acid analog, H is a heparin residue, $S^1$ is a first spacer, $S^2$ is a second spacer, T is a targeting moiety, m is an integer of about 0 to about 50, and n is an integer of 0 to about 10, with the proviso that both m and n cannot be 0, wherein B and $S^1$ are bonded to each other through a 3-carbon of B, and $S^1$ and $S^2$ can be the same or different.

Typically, m is about 1 to about 30, and even more typically m is about 1 to about 10. In yet another illustrative embodiment of the invention, n is about 1 to about 10.

The heparin can comprise heparin of any type, such as unfractionated heparin, high molecular weight heparin, low molecular weight heparin, heparin fragments, recombinant heparin, heparin analogs, heparan sulfate, and sulfonated polysaccharides containing heparin activity, and the like. The spacers, S1 and S2, are independently selected from the group consisting of alkyl chains, polyethylene glycol, an ethylene diamine residue, and the like. The targeting moiety may comprise a folic acid residue, a cRGD residue, and the like.

An illustrative composition according to the present invention comprises a composition wherein B is a taurocholate residue, H is a low molecular weight heparin residue, $S^1$ and $S^2$ are ethylene diamine residues, and T is a cRGD residue. Another illustrative composition according to the present invention comprises a composition wherein B is a lithocholate residue, H is a low molecular weight heparin residue, $S^1$ and $S^2$ are ethylene diamine residues, and T is a folate residue.

Another illustrative embodiment according to the present invention comprises a composition comprising at least one sulfonated moiety, such as naphthalene trisulfonate, covalently bonded to heparin. Other sulfonated moieties that can be substituted for naphthalene trisulfonate include analogs of naphthalene trisulfonate, other sulfonated naphthalenes, and the like.

Still another illustrative embodiment according to the present invention comprises a composition comprising heparin bonded to the 3-carbon of a bile acid or bile acid analog. Illustratively, the bile acid analog comprises a sulfonate group. The composition may further comprise a first spacer between heparin and the bile acid or bile acid analog, such as an ethylene diamine residue, an alkyl chain, polyethylene glycol, and the like. The composition may also further comprise a targeting moiety coupled to the heparin through a second spacer.

Yet another illustrative embodiment of the invention comprises a method of treating cancer comprising administering to an individual in need thereof an effective amount of a composition represented by the formula

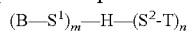
$(B-S^1)_m-H-(S^2-T)_n$ wherein B is a bile acid residue or a bile acid analog, H is a heparin residue, $S^1$ is a first spacer, S2 is a second spacer, T is a targeting moiety, m is an integer of about 0 to about 50, and n is an integer of 0 to about 10, with the proviso that m and n cannot both be 0, and wherein B and $S^1$ are bonded to each other through a 3-carbon of B, and $S^1$ and $S^2$ can be the same or different.

Still another illustrative embodiment of the invention comprises a method of treating cancer comprising administering to an individual in need thereof an effective amount of a composition comprising heparin bonded to the 3-carbon of a bile acid or bile acid analog.

Another illustrative embodiment of the invention comprises a method of making a heparin-spacer-bile acid or heparin-spacer-bile acid analog conjugate. The method comprises first activating the 3-carbon of a bile acid or bile acid analog to result in an activated bile acid or activated bile acid analog. Next, a first spacer is bonded to the activated bile acid or activated bile acid analog to result in a spacer-bile acid or spacer-bile acid analog. Heparin is activated by reacting the heparin with an activating agent to result in an activated heparin. Finally, the activated heparin is bonded to the spacer-bile acid or spacer-bile acid analog to result in the heparin-spacer-bile acid or heparin-spacer-bile acid analog conjugate.

Still another illustrative embodiment of the invention comprises a method of making a heparin-spacer-bile acid-spacer-targeting moiety or heparin-spacer-bile acid analog-spacer-targeting moiety conjugate. The method comprises reacting a targeting moiety with an activating agent to result in an activated targeting moiety. Then, a second spacer is bonded to the activated targeting moiety to result in a second spacer-targeting moiety. Finally, the second spacer-targeting moiety is bonded to the previously described heparin-spacer-bile acid conjugate or heparin-spacer-bile acid analog conjugate to result in the heparin-spacer-bile acid-spacer-targeting moiety conjugate or heparin-spacer-bile acid analog-spacer-targeting moiety conjugate.

As described above, the present invention is drawn to heparin conjugates and methods of making and using them. These conjugates and methods are illustrated in the following examples, which are not to be construed as limiting the claims.

EXAMPLE 1

Synthesis of Heparin-Taurocholic Acid ("HT") Conjugates

Taurocholic acid (TCA)-LMWH was synthesized by conjugating carboxyl groups of LMWH with amine groups of TCA-amine derivatives. First, taurocholic acid nitrophenyl carbonate was synthesized (CB-TCA; FIG. 1), which comprises an activated derivative of taurocholic acid. TCA sodium salt (0.5 g; Sigma Chemical Co., St. Louis, Mo.) was mixed with N,N-dimethylformamide (DMF; 4.6 ml; Sigma), and the mixture was agitated at 0° C. Then, triethylamine (0.565 g; Sigma) and 4-nitrophenyl chloroformate (NPC; Sigma) were added to the mixture and reacted for 1 h at 0° C. followed by 6 h at room temperature. This resulted in the 4-nitrophenyl formate group bonding to the 3-hydroxyl group of TCA. The feed mole ratio of TCA, NPC, and triethylamine was 1:5:6.

Figure 2:
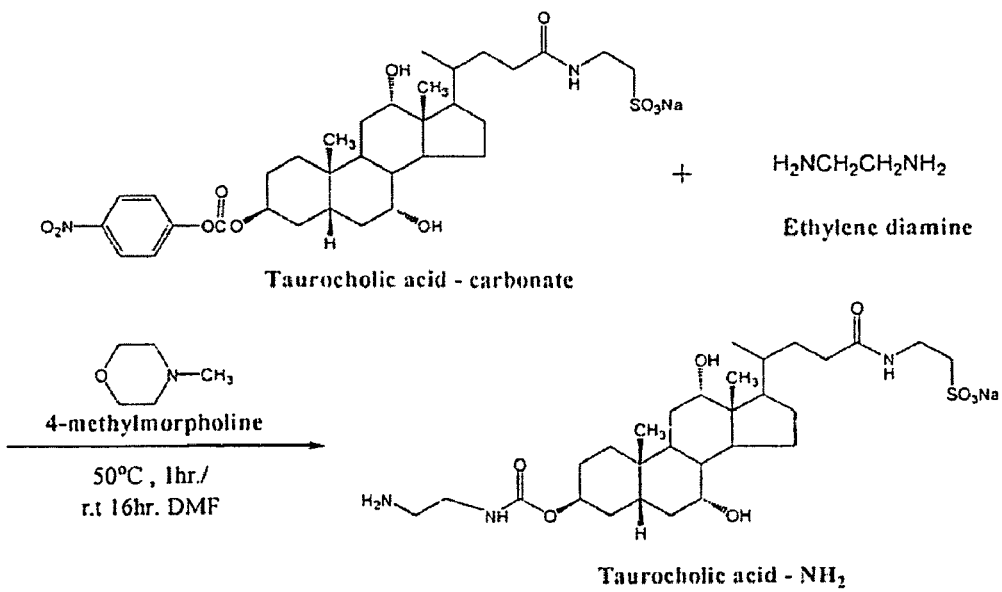
FIG. 2 illustrates a scheme for synthesis of an ethylene amine derivative of taurocholic acid (Et-TCA) by reaction of CB-TCA with ethylene diamine such that the ethylene diamine replaces the 4-nitrophenyl group.

Second, an amine derivative of taurocholic acid (Et-TCA) was synthesized (FIG. 2). CB-TCA (0.5 g) was dissolved in 5 ml of DMF. Then, 4-methyl-morpholine (0.144 g; Sigma) was added, followed by agitation for 1 h at 50° C. This solution was slowly added to an excess of ethylenediamine, followed by agitation for 16 h at room temperature. The feed mole ratio of CT-TCA, 4-methylmorpholine, and ethylenediamine was 1:2:100. Since ET-TCA was water soluble, but ethylenediamine, 4-methylmorpholine, and NPC were not, acetone recrystallization was used to obtain pure Et-TCA., which was then dried under partial vacuum.

Figure 3:
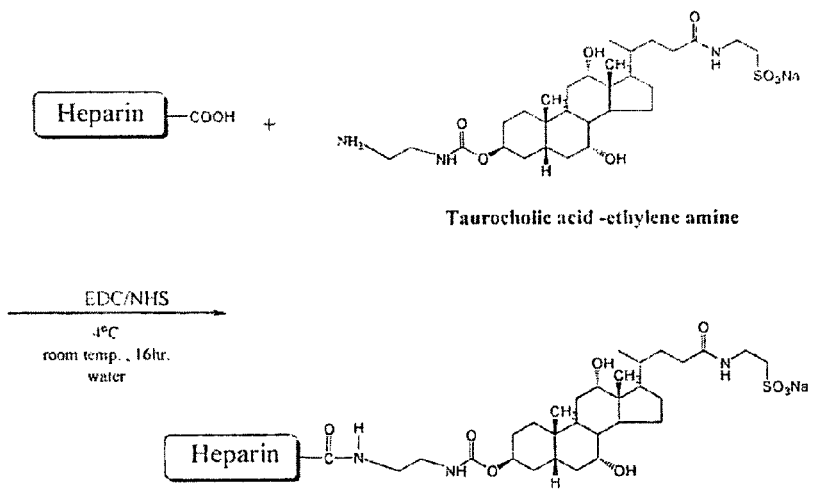
FIG. 3 illustrates a scheme for synthesis of a heparin-taurocholic acid conjugate by reaction of ET-TCA with heparin such that a carboxyl group on heparin bonds to the free amine group of ET-TCA, resulting in heparin conjugated to taurocholic acid through the 3-carbon thereof.

Finally, ET-TCA was conjugated to heparin (FIG. 3). LMWH (Fraxiparin; average molecular weight, 4500 Da; Sanofi-Synthelabo Co., Gentilly, France) was dissolved in distilled water. A carboxyl group of LMWH was activated by adding 1-ethyl-3-(3-dimethylaminopropyl)carbodiimidehydrochloride (EDC; Sigma) with chilling in an ice bath and agitation for 5 min. N-Hydroxysuccinimide (NHS(HOSu); Sigma) was then added to this solution and agitated for 30 min. Finally, ET-TCA was added slowly, then the reaction was carried out at room temperature overnight. The reaction was then dialyzed overnight to remove unreacted EDC, NHS (HOSu), and ET-TCA. Several preparations of heparin taurocholate (HT) were made by controlling the feed mole ratio, as shown in Table 1. These preparations were named HT1, HT2, HT3, and so forth. The coupling ratio and anticoagulant activity of each preparation were determined. Coupling ratio is expressed as the number of taurocholate moieties per heparin. Anticoagulant activity is expressed as the percent of activity of dialyzed LMWH, as determined with an FXa kit from Sigma.

TABLE 1

|  | HT1 | HT2 | HT3 | HT4 | HT5 | HT10 |
| --- | --- | --- | --- | --- | --- | --- |
| Fraxiparin | 1 | 1 | 1 | 1 | 1 | 1 |
| EDC | 1.2 | 2.4 | 3.6 | 4.8 | 6.0 | 12.0 |
| NHS (HOSu) | 1.2 | 2.4 | 3.6 | 4.8 | 6.0 | 12.0 |
| Et-TCA | 1.3 | 2.7 | 4 | 5.3 | 6.7 | 13.3 |
| Coupling ratio | 0.8817 | 2.0800 | 2.9201 | 3.7980 | 3.9707 | 7.4721 |
| Anticoagulant activity | 90.54 | 80.69 | 31.319 | 22.10 | 17.81 | 12.68 |

EXAMPLE 2

Synthesis of Heparin-Lithocholic Acid ("HL") Cojugates

A solution of lithocholic acid (LITHO; 23. 5 mmol; Sigma) in 25 ml of methanol was acidified 2 with 0.3 ml of concentrated HCl. This mixture was stirred and heated to reflux at 75° C. for 6 h. The solution was then cooled to 0° C. until crystallization occurred. The product was thrice filtered and washed with cold methanol, followed by vacuum drying at room temperature. The resulting lithocholyl methyl ester (3.8 g) was reacted with 75 ml of ethylenediamine by reflux at 120° C. for 7 h. After cooling to room temperature, the mixture was precipitated in cold distilled water with vigorous stirring, stored at 0° C. for 1 day, filtered, and washed with cold distilled water. The white powder LITHO-NH2 was obtained after drying under partial vacuum.

Heparin (100 mg) was dissolved in 3 ml of formamide by gentle heating. Different amounts of EDC were mixed with heparin solutions at room temperature, followed by the addition of different amounts of LITHO-NH$_2$ dissolved in DMF with slight heating. The reaction was performed at room temperature for 24 h. The product was precipitated in excess cold acetone, and precipitates were stored at 0° C., washed 5 times with cold acetone to remove unreacted LITHO-NH$_2$, followed by drying under reduced pressure. The resulting precipitates were collected by lyophilization to give heparin-lithocholic acid derivatives.

EXAMPLE 3

Synthesis of Folate-HL Derivatives

Folic acid (1 mmol; Sigma) was dissolved in 20 ml of dimethylsulfoxide (DMSO) with gentle heating (above 50° C.). N,N-dicyclohexylcarbodiimide (DCC; Sigma) and HOSu (2 mmol) were then added to the solution and reacted in the dark for 6 h. After removing precipitants (dicyclohexyl urea) by filtration, the resulting folate-NHS was mixed with 13 mmolar equiv of ethylenediamine plus 500 µl of pyridine and allowed to react at room temperature overnight. The crude product was precipitated by addition of excess acetonitrile, filtered, and washed 10 times with diethyl ether before drying under reduced pressure. For further purification, gamma-linked folate-NH$_2$ was separated from the unwanted folic acid by HPLC.

HL was dissolved in 20 ml of formamide (Sigma) with EDC (3.38 mg) with 5 µl of DIEA for 24 h. The gamma-linked folate-NH$_2$ (16 mg) dissolved in 2 ml of DMF was then added to the reaction plus TEA (16.5 µl) for 20 h. The unreacted folate-NH$_2$ was removed by dialysis (MWCO 2000). The final yellowish product, folate-HL ("FHL"), was obtained by lyophilization.

EXAMPLE 4

Synthesis of Heparin-DOCA (HD) Conjugates

Figure 4:
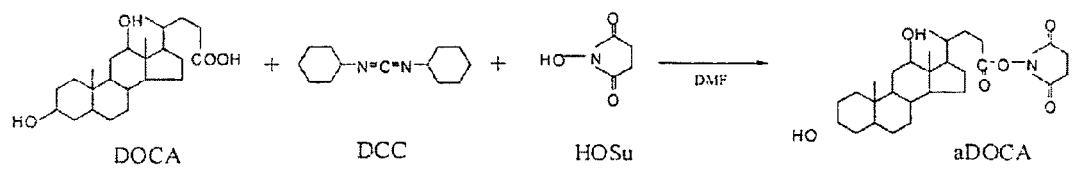
FIG. 4 illustrates a scheme for synthesis of activated deoxycholic acid (aDOCA) from deoxycholic acid (DOCA).

First, deoxycholic acid (DOCA) was activated to result in activated deoxycholic acid (aDOCA) according to the procedure illustrated in FIG. 4. DOCA (Sigma) was mixed with DCC (7.4 g) and NHS (4.5 g) in 100 ml of tetrahydrofuran (THF). The mixture was reacted for 12 h at room temperature under a nitrogen atmosphere, then the precipitated dicyclohexylurea was removed by filtration. The filtrate was precipitated in n-hexane. The succinimido DOCA precipitate was filtered off and washed thoroughly with n-hexane, followed by vacuum drying at room temperature.

Figure 5:
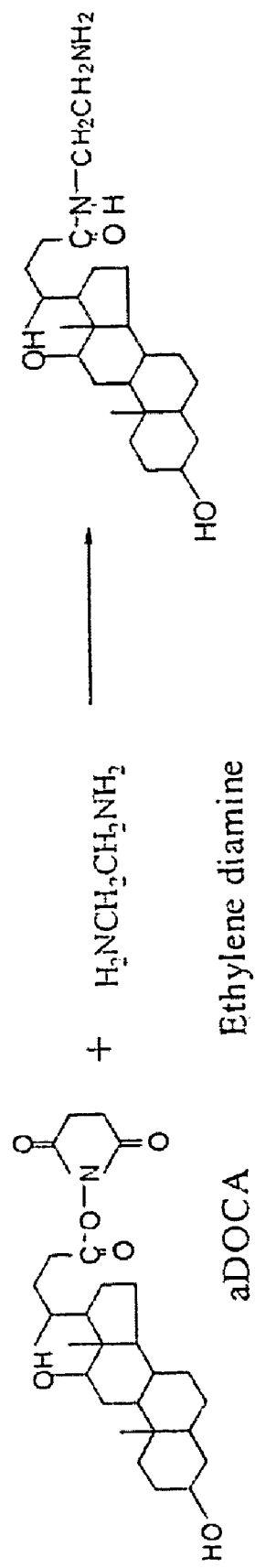
FIG. 5 illustrates a scheme for synthesis of N-deoxycholyl-ethylenediamine from aDOCA.

Next, aDOCA was converted to N-deoxycholylethylenediamine according to the procedure illustrated in FIG. 5. N-Deoxycholylethylenediamine (DOCA-NH$_2$) was synthesized by introducing ethylenediamine to the activated (with a succinimido group) DOCA. Succinimido DOCA (1 g) was dissolved in DMF (5 ml), and the solution was slowly added dropwise into ethylenediamine (13.4 ml) solution. After reaction for 6 h, the mixture was precipitated in distilled water. The white powder DOCA-NH$_2$ was obtained after washing 3 times with distilled water and drying at reduced pressure.

Figure 6:
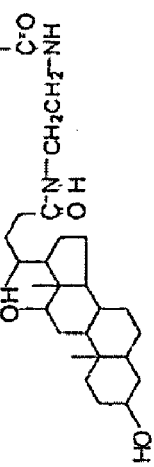
FIG. 6 illustrates a scheme for synthesis of a heparin-DOCA conjugate from N-deoxycholylethylenediamine and heparin.
Figure 6:
Figure 6:
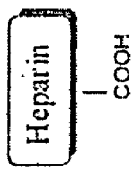
Figure 6:
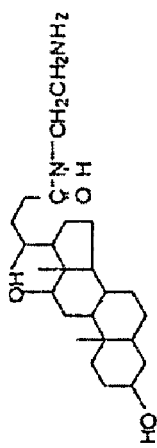

Finally, heparin was conjugated to N-deoxycholylethylenediamine according to the procedure illustrated in FIG. 6. Heparin (0.1 g) was dissolved in formamide (5 ml) with gentle heating. Different amounts of EDC were mixed with heparin solutions at room temperature, followed by addition of different amounts of DOCA-NH$_2$ dissolved in DMF. The resulting solutions were stirred at room temperature under a nitrogen atmosphere for 24 h. After mixtures were precipitated in cold acetone, precipitates were carefully washed 3 times with acetone to remove excess DOCA-NH$_2$, followed by drying at reduced pressure. The dried HD conjugates were dissolved in water. Lyophilization of the HD conjugates provided a white powder.

EXAMPLE 5

Analysis of Heparin Derivatives

Heparin derivatives prepared according to the procedures of Examples 1-4 were analyzed using IR and H$^1$-NMR (JEOLJNM-LA300 WB FT-NMR/FT-IR, Tokyo, Japan), which was operated in deuterium-substituted proper solvents. The NMR data show that taurocholic acid was successfully conjugated to LMWH, and the HPLC data show the purity of the synthesized materials that were used as intermediates in the synthesis reactions.

As used herein, "heparin activity" means the anticoagulation ability of heparin. The COATEST HEPARIN FXa assay kit from Chromogenix was used for determining heparin activity of heparin conjugates. Results were recorded at 405 nm.

The size of self-aggregated dispersions was determined using dynamic light scattering (Spectra Physics Laser Model 127-35) operated at 633 nm and 25±0.1° C. Scattered light was measured at an angle of 90° and collected with a BI-9000 At autocorrelator. The concentration of HD conjugates was kept constant at 1 mg/ml. The hydrodynamic diameter of self-aggregates was calculated by the Stokes-Einstein equation. The polydispersity factor, represented as $\mu_2/\Gamma^2$ was evaluated from the cumulant method, where $\mu_2$ is the second cumulant of the decay function and $\Gamma$ is the average characteristic line width. The zeta potentials of the nanoparticles were measured using an ELS-8000 electrophoretic light scattering spectrophotometer (Otsuka Electronics Co., Ltd., Japan).

The ultra-violet circular dichroism (CD) spectrum of proteins can predict important characteristics of their secondary structure. CD spectra can be readily used to estimate the fraction of a molecule that is in the alpha-helix conformation, the beta-sheet conformation, the beta-turn conformation, or some other (e.g., random coil) conformation. Jasco J-715 Circular Dichroism (Jasco, Japan) was used for making the determination.

Table 2 shows the characterization of heparin derivatives prepared according to Examples 1-4.

TABLE 2

| Sample | Feed mole ratio | DS | Mn | anticoagulation activity (%) | | cac (mg/ml) | d (nm) | ζ (mV) |
| | | | | FXa | APTT | | | |
| --- | --- | --- | --- | --- | --- | --- | --- | --- |
| HD1 | 1:20.0:81.6 | 6.2 | 14,700 | 62 | 63 | 0.02 | 200 | −55.6 |
| HD2 | 1:30.0:122.0 | 8.0 | 15,480 | 51 | 54 | 0.01 | 150 | −57.4 |

TABLE 2-continued

| Sample | Feed mole ratio | DS | Mn | anticoagulation activity (%) | | cac (mg/ml) | d (nm) | ζ (mV) |
| --- | --- | --- | --- | --- | --- | --- | --- | --- |
| | | | | FXa | APTT | | | |
| HD3 | 1:50.0:203.2 | 9.6 | 16,350 | 37 | 42 | 0.003 | 120 | −56.3 |
| HD4 | 1:60.0:244.0 | 11.1 | 16,990 | 23 | 27 | 0.0025 | 109 | −55.9 |
| HL8 | 1:30:60 | 8.6 | 15,480 | 70 | — | 0.015 | 169 | −51.7 |
| HL11 | 1:60:120 | 11.5 | 16,640 | 37 | — | 0.009 | 164 | −50.1 |
| HL12 | 1:100:200 | 12.4 | 17,030 | 10 | — | 0.006 | 171 | −47.6 |
| HL13 | 1:140:280 | 13.4 | 17,420 | 3 | — | 0.004 | 197 | −42.9 |

EXAMPLE 6

Tumor Growth Inhibition

Figure 7:
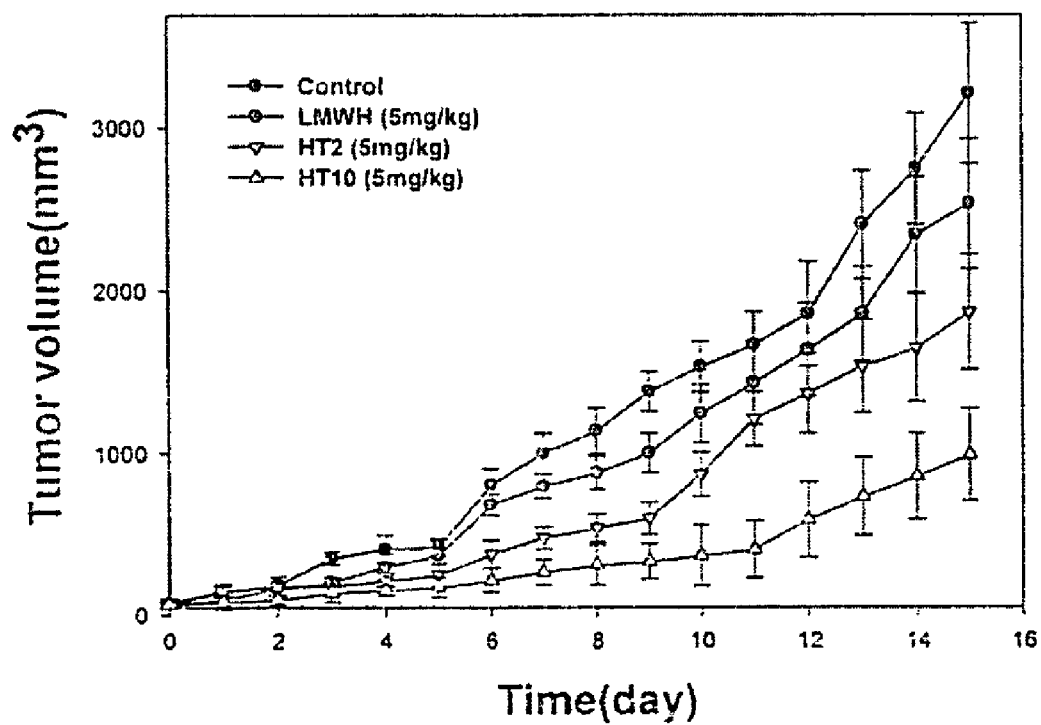
FIG. 7 shows tumor volume as a function of days after inoculation of C3H/HeN mice with LMWH (5 mg/kg), HT10 (5 mg/kg), HT2 (5 mg/kg), and a control.

The anti-tumor activity of LMWH, HT10, HT2, and control were compared in a tumor volume inhibition study. Seven-week-old male C3H/HeN mice (Orient Bio) were used for all animal experiments. Subcutaneous tumors were established by inoculating $1\times10^6$ SCC cells in the backs of the mice by subcutaneous injection. Care and maintenance of animals were performed in adherence to institutional guidelines of the Institutional Animal Care and Use Committee (IACUC). When the tumors had grown to about 50-70 mm³, the mice were given intravenous injections of 0.1 ml of saline containing HT 10 (5 mg/kg), HT2 (5 mg/kg), or LMWH (5 mg/kg), or saline alone (control), every three days. On the 15th day, the mice were sacrificed and their tumors removed. All treatment groups contained 7 or 8 mice. Tumor tissues were isolated from three representative treated and untreated tumor-bearing mice. Detection of microvessels and expression of the proliferating cell nuclear antigen (PCNA) marker in tumor tissues were carried out by immunohistochemistry using a specific anti-CD34 antibody and anti-PCNA antibody (Dako, Carpinteria, Calif.), respectively. FIG. 7 shows that HT10 resulted in about 69% tumor volume inhibition compared to the control treatment.

EXAMPLE 7

Figure 8:
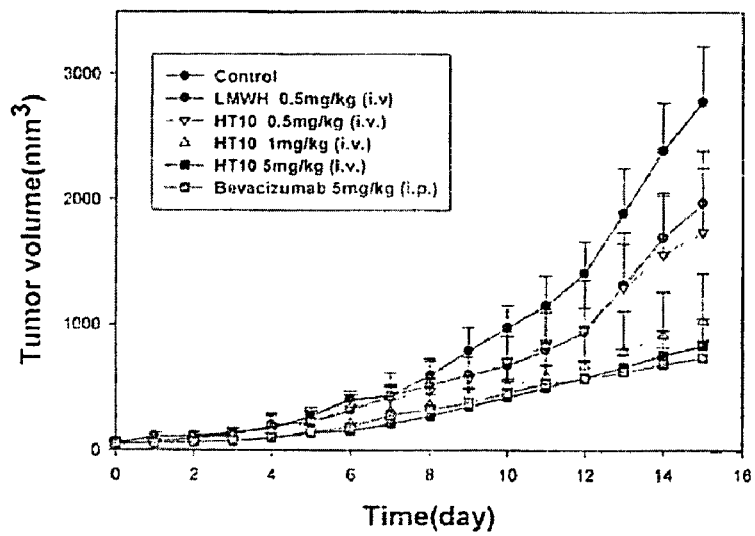
FIG. 8 shows tumor volume as a function of days after inoculation of C3H/HeN mice with LMWH (0.5 mg/kg), HT10 (0.5 mg/kg), HT10 (1 mg/kg), HT10 (5 mg/kg), bevacizumab (5 mg/kg), and a control.

The procedure of Example 6 was followed, except that HT10 (5 mg/kg), HT10 (1 mg/kg), HT10 (0.5 mg/kg), LMWH (0.5 mg/kg), and control were intravenously administered daily, and bevacizumab (5 mg/kg) was intraperitoneally administered twice weekly. HT 10 is a nontoxic heparin derivative, and its anticoagulation activity is less than 13% that of LMWH, thus daily administration was not problematic. FIG. 8 shows that HT10 administered in doses of 1 mg/kg and 5 mg/kg was similar in its tumor growth inhibition effect to bevacizumab. HT 10 (5 mg/kg) inhibited tumor growth about 71% compared with the control, while HT10 (1 mg/kg) inhibited tumor growth about 63%, and bevacizumab inhibited tumor growth about 74%. Neither HT10 nor LMWH administered at 0.5 mg/kg were effective in inhibiting tumor growth.

EXAMPLE 8

Figure 9:
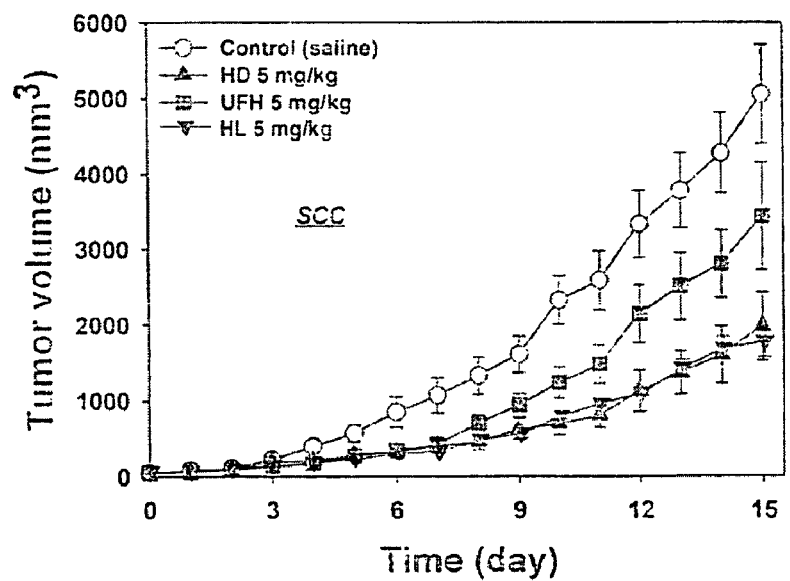
FIG. 9 shows tumor volume as a function of days after inoculation of C3H/HeN mice with HD (5 mg/kg), UFH (5 mg/kg), HL (5 mg/kg), and a saline control.

The procedure of Example 6 was followed except that UFH (5 mg/kg), HL (5 mg/kg), HD (5 mg/kg), and a control were administered. As shown in FIG. 9, HD and HL exhibited about 55-60% tumor volume inhibition compared with the control.

EXAMPLE 9

Figure 10:
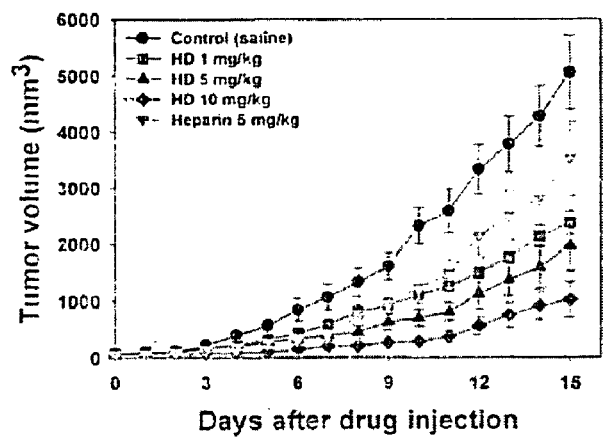
FIG. 10 shows tumor volume as a function of days after inoculation of C3H/HeN mice with HD (1 mg/kg), HD (5 mg/kg), HD (10 mg/kg), heparin (5 mg/kg), and a saline control.
Figure 11:
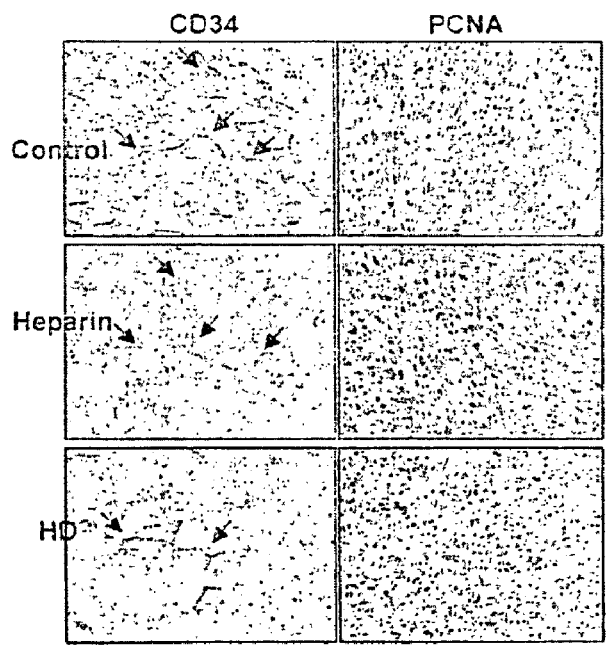
FIG. 11 shows detection of microvessels and expression of the proliferating cell nuclear antigen (PCNA) in tumor tissues treated with a control, heparin, or HD, as detected by immunohistochemistry using either an anti-CD34 antibody or and anti-PCNA antibody.

HD was selected for a study on the in vivo dose effect of this heparin conjugate. The procedure of Example6 was carried out, except that treatments were HD (10 mg/kg), HD (5 mg/kg), HD (1 mg/kg), heparin (5 mg/kg), and control. Detection of microvessels and expression of PCNA was carried out using immunohistochemistry and anti-CD34 antibody and anti-PCNA antibody (Dako). Results are shown in FIGS. 10 and 11.

EXAMPLE 10

Figure 12:
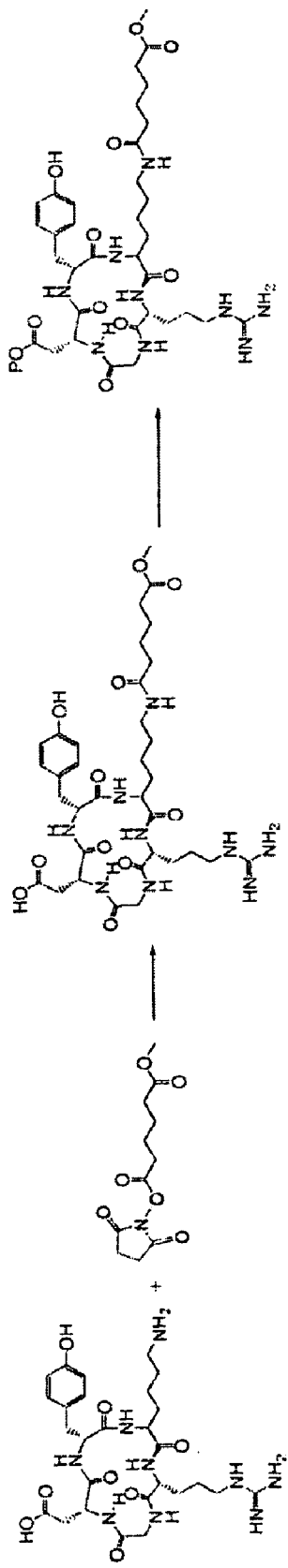
FIGS. 12-14 illustrate a scheme for synthesis of a cRGDyK-heparin-taurocholic acid conjugate.
Figure 13:
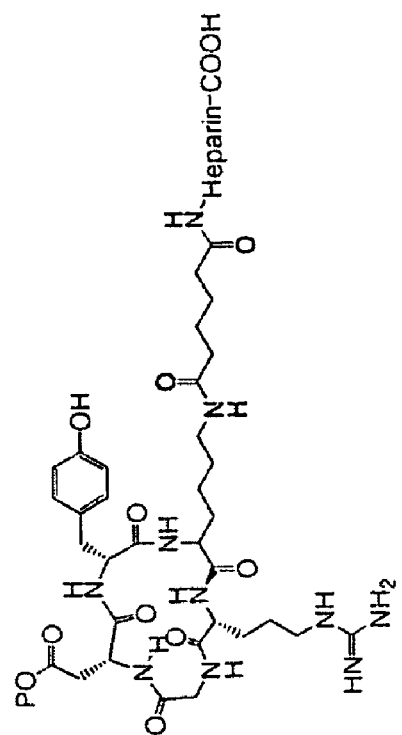
Figure 13:
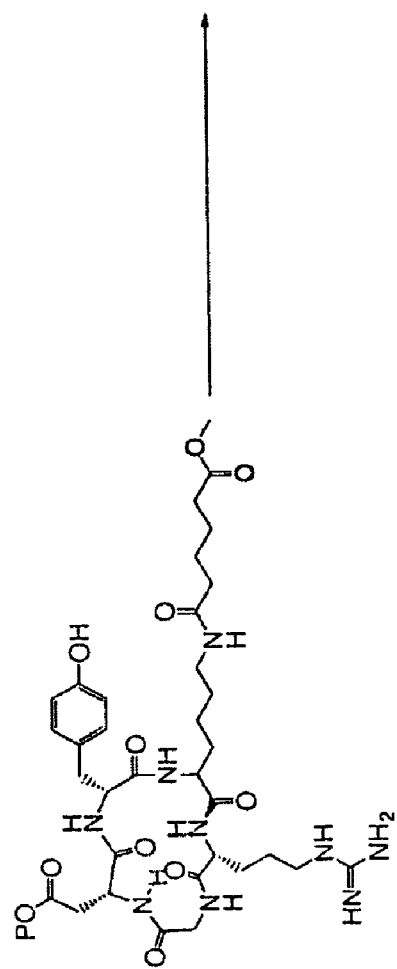
Figure 14:
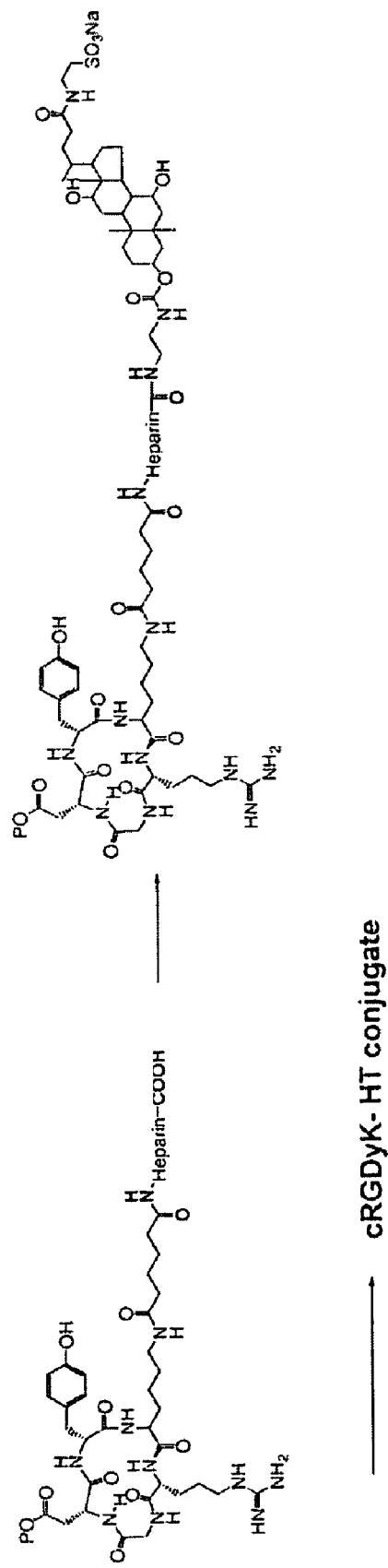

FIGS. 12-14 show synthesis of a cRGD-HT conjugate. First, 50 mg of cRGDyK peptide was dissolved in DMF (10 ml) and then methyl-N-succinimidyl adipate (MSA, 32 mg) was added. After stirring for 12 h at room temperature, phenyl ester was added to the reaction mixture and stirring was continued for 6 h to protect the carboxyl group of the cRGDyK peptide. Next, the reaction mixture was precipitated with a 3-fold excess of water to remove any unreacted reagents, and the precipitate was washed with water and then dried in vacuo.

The resulting MSA-linked cRDG (4.2 mg) was dissolved in DMF (1 ml) and was mixed with end-aminated heparin (100 mg) dissolved in formamide (7 ml) and stirred in the presence o sodium cyanide for 24 h. The reaction mixture was then precipitated in cold acetone, and the precipitate was washed with acetone several times. After completely evaporating the acetone, the precipitate was dissolved in distilled water and then lyophilized.

Next, the cRDG-coupled heparin (50 mg) was dissolved in 10 ml of distilled water and 1-ethyl-3-(3-dimethylaminopropyl) carbodiimide (EDAC;10.6 mg) was then added. The, ET-TCA (47.4 mg), prepared according to the procedure of Example 1 was added to the heparin solution. The pH was adjusted to 5.0 with 1 N HCl. After stirring for 12 h at room temperature, hydrogen peroxide was added to the reaction mixture, which was incubated for 6 h. The reaction mixture was then dialyzed using 2000 MWCO dialysis membrane and lyophilized.

EXAMPLE 11

Figure 15:
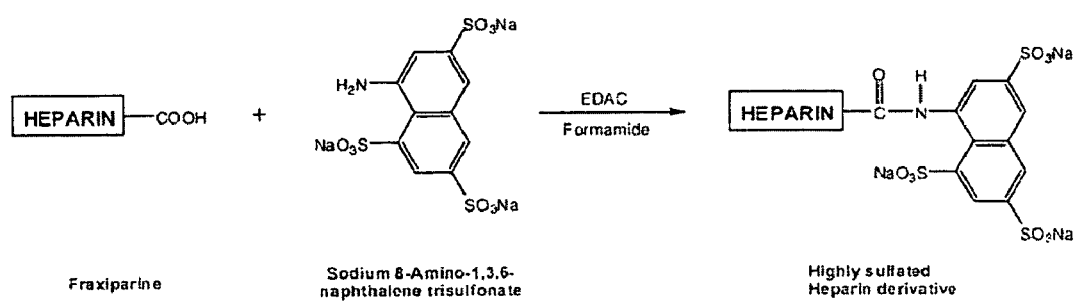
FIG. 15 illustrates a scheme for synthesis of a highly sulfated heparin derivative, namely, a heparin-naphthalene trisulfonic acid conjugate.

Highly sulfated heparin derivatives were prepared according to the scheme illustrated in FIG. 15 and Table 3.

First, heparin (Fraxiparine) in an amount indicated in column A was dissolved in the corresponding amount of formamide from column B, and this solution was agitated on an ice bath. Next, EDAC in the corresponding amount from column C was added to the heparin solution. Then, trisodium 8-amino-1,3,6-naphthalene trisulfonate (ANTS) in the corresponding amount from column D dissolved in the corresponding amount of formamide from column E was mixed with the activated heparin solution. After stirring for 12 h at room temperature, the reaction mixture was dialyzed against water using a 1000 MWCO membrane for 2 days and was then lyophilized. The amount of naphthalene trisulfonate in the resulting heparin derivative was determined by HPLC, and the anti-coagulation activity of this highly sulfated heparin derivative was evaluated using an anti-FXa chromogenic assay.

TABLE 3

| Mole Ratio | | | A | B | C | D | E |
|---|---|---|---|---|---|---|---|
| Heparin (LMWH) | EDAC | ANTS | Heparin (mg) | Formamide (ml) | EDAC (mg) | ANTS (mg) | Formamide (ml) |
| 1 | 1.2 | 1 | 100 | 3.125 | 5.112 | 9.496 | 0.993 |
| 1 | 2.4 | 2 | 100 | 3.125 | 10.225 | 18.993 | 1.866 |
| 1 | 3.6 | 3 | 100 | 3.125 | 15.337 | 28.489 | 2.800 |
| 1 | 6 | 5 | 100 | 3.125 | 25.561 | 47.482 | 4.666 |
| 1 | 8.4 | 7 | 100 | 3.125 | 35.786 | 66.475 | 6.532 |
| 1 | 12 | 10 | 100 | 3.125 | 51.123 | 94.964 | 9.332 |
| 1 | 18 | 15 | 100 | 3.125 | 76.684 | 142.447 | 13.998 |

EXAMPLE 12

Folate-heparin-lithocholate (FHL) was prepared as follows. Folic acid (1 mmol) dissolved in 20 ml DMSO was reacted with DCC (1.2 mmol) and NHS (2 mmol) at 50° C. for 6 h. Folate has two α- and γ-carboxylic acids, but the γ-carboxylic acid is more selectively activated due to its higher reactivity. The resulting folate-NHS was reacted with ethylene diamine (13 mmol) and pyridine (500 mg) at room temperature overnight. The folylethylamine (folate-$NH_2$) was precipitated by the addition of excess acetonitrile, and the precipitate was filtered and washed with diethyl ether before trying under vacuum to get yellow powder. This product was added to HL (100 mg), dissolved in 20 ml of formamide, and activated by EDAC (3.38 mg) with 5 µl of N,N-diisopropylethylamine (DIEA) for 12 h. The unreacted folate-NH2 was removed by dialysis (MWCO 2000). The final product, FHL, was obtained by lyophilization at a yield of 97%. The folate content in FHL was determined by quantitative UV spectrophotometry at 365 nm. The anti-coagulation activity of FHL was measured by Fxa chromogenic assay (COATEST®Heparin, Milan, Italy).

The subject matter claimed is:

1. A composition comprising a heparin bonded to the 3-carbon of a bile acid or a bile acid analog wherein the bile acid analog comprises a sulfonate group, wherein the bile acid is a member selected from cholic acid, deoxycholic acid, chenodeoxycholic acid, lithocholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid.

2. The composition of claim 1 further comprising a spacer between the heparin and the bile acid or bile acid analog.

3. The composition of claim 2 wherein the spacer is a member selected from alkyl chains, polyethylene glycol, and an ethylene diamine residue.

4. The composition of claim 1 wherein the heparin is a member selected from unfractionated heparin, high molecular weight heparin, low molecular weight heparin, heparin fragments, recombinant heparin, heparin analogs, heparan sulfate, and sulfonated polysaccharides containing heparin activity.

5. A composition represented by the formula

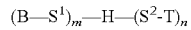

wherein B is a bile acid residue selected from cholic acid, deoxycholic acid, chenodeoxycholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid or a bile acid analog comprising a sulfonate group, H is a heparin residue, $S^1$ is a first spacer, $S^2$ is a second spacer, T is a targeting moiety, m is an integer of 1 to about 30, and n is an integer of 1 to about 10, and wherein B and $S^1$ are bonded to each other through a 3-carbon of B, and $S^1$ and $S^2$ can be the same or different.

6. The composition of claim 5 wherein B is a deoxycholic acid residue.

7. The composition of claim 5 wherein B is a taurocholic acid residue.

8. The composition of claim 5 wherein said heparin residue is a member selected from unfractionated heparin, high molecular weight heparin, low molecular weight heparin, heparin fragments, recombinant heparin, heparin analogs, heparan sulfate, and sulfonated polysaccharides containing heparin activity.

9. The composition of claim 5 wherein H is low molecular weight heparin.

10. The composition of claim 5 wherein $S^1$ and $S^2$ are independently selected from the group consisting of alkyl chains, polyethylene glycol, and an ethylene diamine residue.

11. The composition of claim 5 wherein T is a folic acid residue.

12. The composition of claim 5 wherein T is a cRGD residue.

13. The composition of claim 5 wherein B is a taurocholate residue, $S^1$ is an ethylene diamine residue, H is low molecular weight heparin, $S^2$ is an ethylene diamine residue, and T is a cRGD residue.

14. The composition of claim 5 wherein B is a deoxycholate residue, $S^1$ is an ethylene diamine residue, H is low molecular weight heparin, $S^2$ is an ethylene diamine residue, and T is a folate residue.

15. A composition comprising a heparin bonded to the 3-carbon of a bile acid and to a targeting moiety, wherein the bile acid is a member selected from cholic acid, deoxycholic acid, chenodeoxycholic acid, lithocholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, and hyodeoxycholic acid.

16. The composition of claim 15 further comprising a spacer between the heparin and the bile acid.

17. The composition of claim 16 wherein the spacer is a member selected from alkyl chains, polyethylene glycol, and an ethylene diamine residue.

18. The composition of claim 15 wherein the heparin is a member selected from unfractionated heparin, high molecular weight heparin, low molecular weight heparin, heparin fragments, recombinant heparin, heparin analogs, heparan sulfate, and sulfonated polysaccharides containing heparin activity.

* * * * *